(12) United States Patent
Radisch, Jr. et al.

(10) Patent No.: US 8,043,259 B2
(45) Date of Patent: Oct. 25, 2011

(54) MEDICAL DEVICE SYSTEMS

(75) Inventors: Herbert R. Radisch, Jr., San Diego, CA (US); Fuh-Sheng Chen, San Diego, CA (US); Show-Mean Wu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1801 days.

(21) Appl. No.: 10/852,631

(22) Filed: May 24, 2004

(65) Prior Publication Data

US 2005/0261721 A1 Nov. 24, 2005

(51) Int. Cl.
*A61M 31/00* (2006.01)
*A61M 37/00* (2006.01)
*A61L 33/00* (2006.01)
*B05D 3/00* (2006.01)

(52) U.S. Cl. .................................. 604/103.08; 427/2.1
(58) Field of Classification Search ............... 604/96.01, 604/192
See application file for complete search history.

(56) References Cited

U.S. PATENT DOCUMENTS

| | | | |
|---|---|---|---|
| 4,273,128 A | 6/1981 | Lary | |
| 4,669,469 A | 6/1987 | Gifford, III et al. | |
| 4,765,332 A | 8/1988 | Fischell et al. | |
| 4,781,186 A | 11/1988 | Simpson et al. | |
| 4,867,157 A | 9/1989 | McGurk-Burleson et al. | |
| 4,887,613 A | 12/1989 | Farr et al. | |
| 4,909,781 A | 3/1990 | Husted | |
| 4,950,277 A | 8/1990 | Farr | |
| 4,963,313 A | 10/1990 | Noddin et al. | |
| 4,966,604 A | 10/1990 | Reiss | |
| 4,986,807 A | 1/1991 | Farr | |
| 5,030,201 A | 7/1991 | Palestrant | |
| 5,074,871 A | 12/1991 | Groshong | |
| 5,176,693 A | 1/1993 | Pannek, Jr. | |
| 5,178,625 A | 1/1993 | Groshong | |
| 5,196,024 A | 3/1993 | Barath | |
| 5,209,799 A | 5/1993 | Vigil | |
| 5,224,945 A | 7/1993 | Pannek, Jr. | |
| 5,226,909 A | 7/1993 | Evans et al. | |
| 5,320,634 A | 6/1994 | Vigil et al. | |
| 5,336,234 A | 8/1994 | Vigil et al. | |
| 5,389,314 A | 2/1995 | Wang | |
| 5,482,740 A | 1/1996 | Conway et al. | |
| 5,556,408 A | 9/1996 | Farhat | |
| 5,616,149 A | 4/1997 | Barath | |
| 5,714,110 A | 2/1998 | Wang et al. | |
| 5,718,684 A | 2/1998 | Gupta | |
| 5,728,123 A | 3/1998 | Lemelson et al. | |
| 5,792,158 A | 8/1998 | Lary | |
| 5,797,935 A | 8/1998 | Barath | |
| 5,833,657 A | 11/1998 | Reinhardt et al. | |
| 5,843,156 A | 12/1998 | Slepian et al. | |
| 5,919,163 A | 7/1999 | Glickman et al. | |
| 5,951,494 A | 9/1999 | Wang et al. | |
| 6,120,364 A | 9/2000 | Laflamme | |
| 6,129,706 A | 10/2000 | Janacek | |
| 6,135,992 A | 10/2000 | Wang | |
| 6,242,063 B1 | 6/2001 | Ferrera et al. | |

(Continued)

OTHER PUBLICATIONS

U.S. Appl. No. 09/950,195, filed Sep. 10, 2001.

(Continued)

*Primary Examiner* — Nicholas D Lucchesi
*Assistant Examiner* — Pritesh Patel
(74) *Attorney, Agent, or Firm* — Seager Tufte Wickhem LLC

(57) ABSTRACT

Medical device systems and related methods are disclosed.

9 Claims, 3 Drawing Sheets

U.S. PATENT DOCUMENTS

| | | |
|---|---|---|
| 6,258,108 B1 | 7/2001 | Lary |
| 6,284,333 B1 | 9/2001 | Wang et al. |
| 6,398,798 B2 | 6/2002 | Selmon et al. |
| 6,533,754 B1 | 3/2003 | Hisamatsu et al. |
| 6,558,734 B2 * | 5/2003 | Koulik et al. ............... 427/2.24 |
| 6,565,527 B1 | 5/2003 | Jonkman et al. |
| 6,632,231 B2 | 10/2003 | Radisch, Jr. |
| 6,730,105 B2 | 5/2004 | Shiber |
| 7,132,469 B2 * | 11/2006 | Guzauskas .................. 524/492 |
| 2002/0010489 A1 | 1/2002 | Grayzel et al. |
| 2002/0165523 A1 | 11/2002 | Chin et al. |
| 2003/0144677 A1 | 7/2003 | Lary |
| 2003/0163148 A1 * | 8/2003 | Wang et al. .................. 606/159 |
| 2004/0127920 A1 | 7/2004 | Radisch, Jr. |

OTHER PUBLICATIONS

International Search Report and Written Opinion, dated Dec. 1 2005: PCT/US2005/018228.

* cited by examiner

MEDICAL DEVICE SYSTEMS

TECHNICAL FIELD

This invention relates to medical device systems and related methods.

BACKGROUND

Balloon catheters can be used for a variety of medical procedures, such as, for example, to widen an occluded body vessel, as in angioplasty, to position a medical device, such as a stent or a graft, or to selectively block a passageway. A balloon catheter may include an inflatable and deflatable balloon positioned on a narrow catheter shaft. Prior to insertion and positioning of the balloon catheter within a patient's body, the balloon is folded around the shaft to reduce the radial profile of the medical device for easy and a traumatic insertion.

During use, for example, in angioplasty, the folded balloon can be positioned at a location in a vessel occluded by a stenosis by threading the balloon catheter over a guide wire placed in the body. The balloon is then inflated by introducing a fluid, such as saline, into the interior of the balloon. Inflating the balloon can radially expand the stenosis so that the vessel can permit an increased rate of blood flow. After use, the balloon is deflated to its reduced radial profile and withdrawn from the body.

In some cases, it is desirable to incise at least a portion of the stenosis prior to radial expansion, thereby further increasing the blood flow rate.

SUMMARY

The invention relates to medical device systems and related methods.

In one aspect, the invention features a system including an expandable medical device having a wall. The wall of the expandable medical device includes a polymeric material and a plurality of particles in the polymeric material. The plurality of particles include a material selected from the group consisting of fumed silica, carbon black and combinations thereof.

In another aspect, the invention features a system including an expandable medical device having a wall. The wall of the expandable medical device includes a polymeric material and a plurality of milled fibers in the polymeric material.

In a further aspect, the invention features a system including an expandable medical device having a wall and a cutting element attached to the wall. The wall includes a polymeric material and a plurality of particles in the polymeric material. Each of the plurality of particles has at least one dimension that is less than about 100 nanometers.

Features and advantages of the invention are in the description, drawings, and claims.

DESCRIPTION OF DRAWINGS

Like reference symbols in the various drawings indicate like elements.

DETAILED DESCRIPTION

Figure 1:
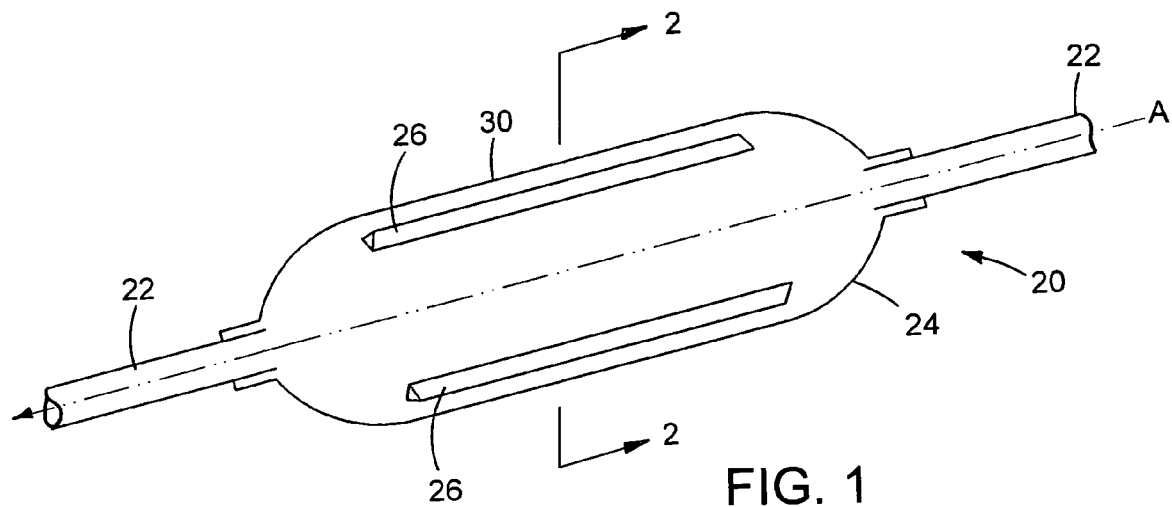
FIG. 1 is an illustration of an embodiment of a medical device system.
Figure 2:
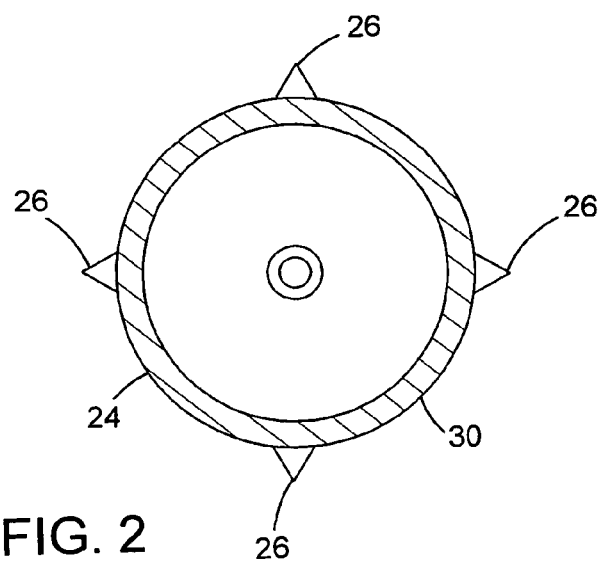
FIG. 2 is a cross sectional view of the medical device system of FIG. 1, taken along line 2-2.

Referring to FIGS. 1 and 2, a balloon catheter 20 for removing stenosis, such as plaque along coronary artery walls, includes a shaft 22, an expandable balloon 24 attached to and in fluid communication with shaft 22, and one or more (here, four) cutting elements 26. The one or more cutting elements 26 are attached to expandable balloon 24 with a bonding material, such as, for example an adhesive or a urethane pad. The use of cutting elements 26 is by way of example only. In general, one or more scoring elements can be used. As referred to herein when carried by a medical device (e.g., balloon catheter 20), a scoring element is capable of scoring and/or cutting stenosis (e.g., plaque along artery walls). In some embodiments, a scoring element can, for example, be in the shape of a wire (e.g., a metal wire, a polymer wire).

Referring particularly to FIG. 2, expandable balloon 24 has a wall 30 that includes one or more layers (here, one). At least one of the layers of wall 30 is formed of a polymeric material(s) and a plurality of additives in the polymeric material(s).

Without wishing to be bound by theory, it is believed that the addition of the additives to the polymeric material(s) enhances the mechanical properties (e.g., stiffness, tensile modulus, and yield stress) of the material forming expandable balloon 24. For example, it is believed that the additives reinforce the polymeric material(s) to strengthen expandable balloon 24 and to increase its puncture resistance. It is also believed that the enhanced mechanical properties are a result of a strong bond (e.g., covalent bond) formed between the additives and the polymeric material. It is further believed that the strong bond is created as a result of the size and/or materials of the additives used in wall 30.

Increasing the stiffness of expandable balloon 24 is believed to reduce the ability of expandable balloon 24 to grow in a longitudinal direction, labeled A in FIG. 1. It is further believed that the reduced ability of expandable balloon 24 to grow can reduce the likelihood of the one or more cutting elements 26 from debonding from expandable balloon 24 during expansion (e.g., inflation of the balloon).

In general, the polymeric material(s) in wall 30 of expandable balloon 24 can be selected as desired. Typically, the polymeric material(s) are selected to be biocompatible with a patient's body. In certain embodiments, the polymeric material(s) are cross-linked. Examples of polymeric material(s) that can be used in wall 30 include polyesters, polyamides, polyurethanes, polycarbonates, and polyolefins. Other examples of polymeric material(s) include ionomers and elastomers. Combinations of polymeric materials can be used as well.

In general, the additives contained within wall 30 can be selected as desired. Typically, the additives are selected to increase the strength (e.g., tensile modulus, yield stress, and puncture resistance) and to reduce longitudinal elongation of expandable balloon 24. In some embodiments, the additives covalently bond to the polymeric material(s) used in wall 30. Examples of additives include particles of fumed silica and carbon black, milled fibers (e.g., milled glass fibers, milled carbon fibers, milled ceramic fibers, milled boron fibers, and milled polymer fibers), and nanosized particulates (e.g., particles that have at least one dimension that is less than about 100 nanometers, such as nanosized clay particles).

Generally, the amount of additive included within wall 30 can be selected as desired. In certain embodiments, the amount of additive included within wall 30 is selected so that the additive is uniformly dispersed within wall 30. In some embodiments, the amount of additive included in wall 30 is at most about 50 weight percent (e.g., at most about 45 weight percent, at most about 40 weight percent, at most about 35 weight percent, at most about 30 weight percent, at most about 25 weight percent) so that the additive can be uniformly dispersed within the polymer material(s).

In certain embodiments, each of the additives are coated with an agent, such as a coupling agent, that covalently bonds to the polymeric material(s) used in wall 30. In some embodiments, the agent is a silane. Examples of silanes that can be used include amino-silanes, methacrylsilanes, hexamethyldisilanes, ureidopropyltriethoxysilanes, glycidyloxypropyltrimethoxysilanes, mercaptopropylmethyldimethoxysilanes, diamino-/alkylfunctional silanes, isocyanatosilanes, alkylalkoxysilanes, vinylfunctional silanes, organosilicone silanes and epoxyfunctional silanes. Combinations of silanes can be used as the agent as well.

In certain embodiments, the additives are treated (e.g., chemically, electrically, is physically) to provide the surface of each of the additives with a functional group. It is believed that the functional group will covalently bond to the polymeric material(s) within wall 30 to provide a strong connection between the additives and the polymer material(s). In some embodiments, the surface of the additives is treated with a plasma, such as a nitrous oxide plasma.

In some embodiments, the additives are sized to provide the additives with a relatively high surface area to mass ratio (e.g., at least about 25 m$^2$/g, at least about 50 m$^2$/g, at least about 75 m$^2$/g, at least about 100 m$^2$/g, at least about 125 m$^2$/g, at least about 150 m$^2$/g, at least about 175 m$^2$/g, at least about 200 m$^2$/g, at least about 225 m$^2$/g, at least about 250 m$^2$/g, at least about 275 m$^2$/g, at least about 300 m$^2$/g, at least about 325 m$^2$/g, at least about 350 m$^2$/g, at least about 375 m$^2$/g, at least about 380 m$^2$/g). It is believed that additives having a relatively high surface area to mass ratio form a strong bond (e.g., covalent bond) with the polymeric material(s) surrounding them. As a result, the additives are incorporated within and reinforce the polymeric material(s) within wall 30.

In general, the material used to form wall 30 can be prepared as desired. In certain embodiments, the material is prepared using twin screw compounding, so that the additives are uniformly dispersed within the polymeric material(s). For example, a material including 80 weight percent of nylon 12 Vestamid L210F (Degussa Corp, Parsippany, N.J.) blended with 20 weight percent hexamethyldisilane coated fumed silica particles (12 nanometers) part number AEROSIL® R8200 (Degussa Corporation, Parsippany, N.J.) can be compounded in a twin screw extruded and chopped into pellets. In certain embodiments, the nylon 12 Vestamid pellets can be cryogenically ground prior to compounding to improve blending of the nylon 12 Vestamid with the fumed silica After compounding, the pellets are then extruded to form a desired tube. In certain embodiments in which wall 30 includes one layer, the tube is extruded using a single extrusion head. In some embodiments in which wall 30 includes multiple layers (e.g., two layers, three layers, four layers, five layers, six layers), the tube is formed using a dual extrusion process as described in U.S. Ser. No. 09/798,749. Other extrusion techniques are described in U.S. Pat. No. 6,242,063 issued to Ferrera, and U.S. Pat. Nos. 6,284,333, 6,135,992, 5,951,494, and 5,389,314 all issued to Wang, and hereby incorporated by reference.

To form expandable balloon 24, the extruded tube can be blow molded. In some embodiments, the tube is placed in a preheated balloon mold, and air is introduced into the tube to maintain the patency of the lumen of the tube. After soaking at a predetermined temperature and time, the tube is stretched for a predetermined distance at a predetermined time, rate, and temperature. The pressure inside the tube is then sufficiently increased to radially expand the tube inside the mold to form the expandable balloon. The formed balloon can be heat treated, for example, to enhance folding memory, and/or folded into a predetermined profile to decrease the likelihood of injury during insertion into a patient. Methods of forming a balloon from a tube are described in, for example, commonly-assigned application U.S. Ser. No. 09/950,195, filed Sep. 10, 2001, and entitled "Medical Balloon;" and commonly-assigned patents U.S. Pat. No. 6,120,364 issued to Anderson, U.S. Pat. No. 5,714,110 issued to Wang, and U.S. Pat. No. 4,963,313 issued to Noddin, all hereby incorporated by reference in their entirety.

After the expandable balloon is formed, one or more cutting elements 26 can be attached to the balloon with an adhesive. In some embodiments, the expandable balloon can be folded over the one or more cutting elements 26 to protect a patient's body from being cut or injured. Folding can be performed during heat treatment of expandable balloon 24, as described in U.S. Pat. No. 5,209,799 issued to Vigil.

In general, expandable balloon 24 can have any of a variety of shapes or sizes. In certain embodiments, expandable balloon 24 can be a coronary balloon, an aortic balloon, a peripheral balloon, a reperfusion balloon, an endoscopy balloon, a gastrointestinal balloon, a urological balloon or a neurological balloon. In some embodiments, balloon 24 has a diameter of at least one millimeter (e.g., at least about two millimeters, at least about three millimeters, at least about four millimeters, at least about five millimeters, at least about six millimeters) when inflated. As an example, balloon 24 can be a peripheral balloon having a diameter of at least about three millimeters (e.g., at least about five millimeters, at least about seven millimeters, at least about nine millimeters, at least about 12 millimeters) when inflated. As another example, balloon 24 can be a urological balloon having a diameter at least about four millimeters (e.g., at least about 10 millimeters, at least about 20 millimeters, at least about 30 millimeters, at least about 40 millimeters) when inflated. As a further example, balloon 24 can be a neurological balloon having a diameter at least about 1.5 millimeters (e.g., at least about two millimeters, at least about three millimeters, at least about four millimeters, at least about five millimeters).

Figure 3A:
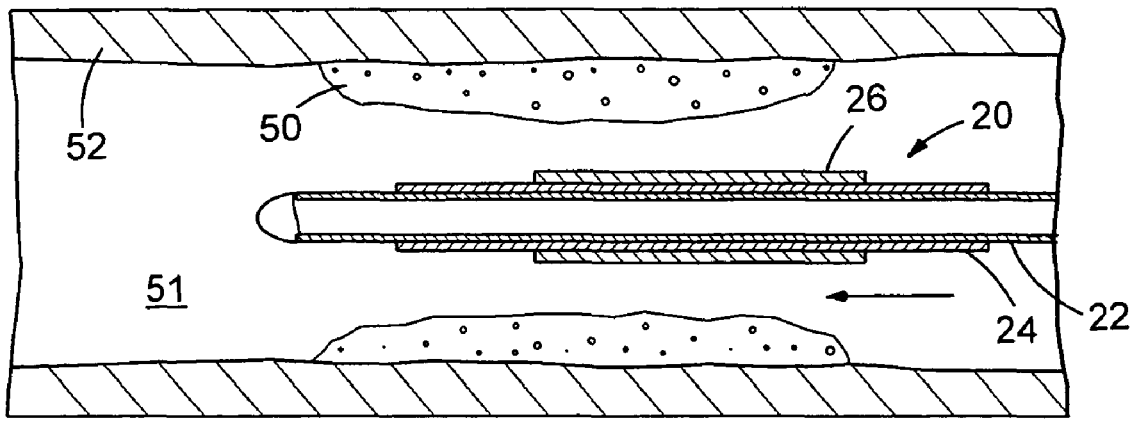
FIGS. 3A, 3B, and 3C illustrate an embodiment of a method of using the medical device system of FIG. 1.
Figure 3B:
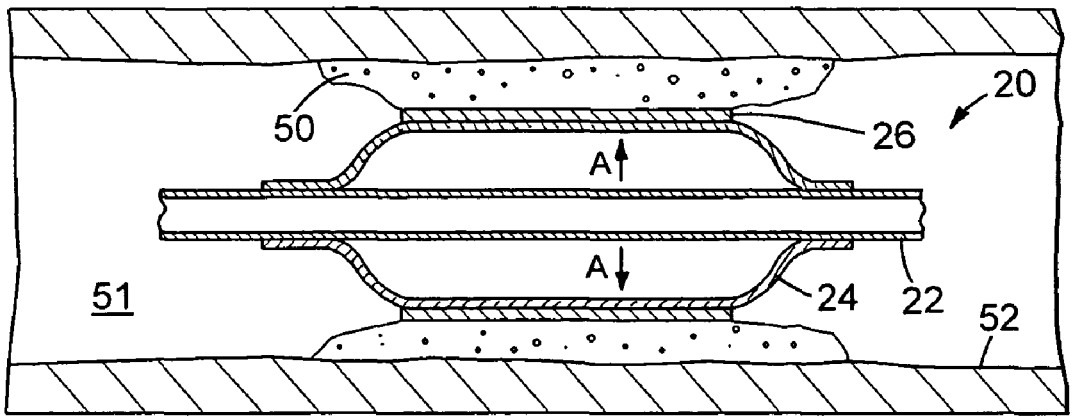
Figure 3C:
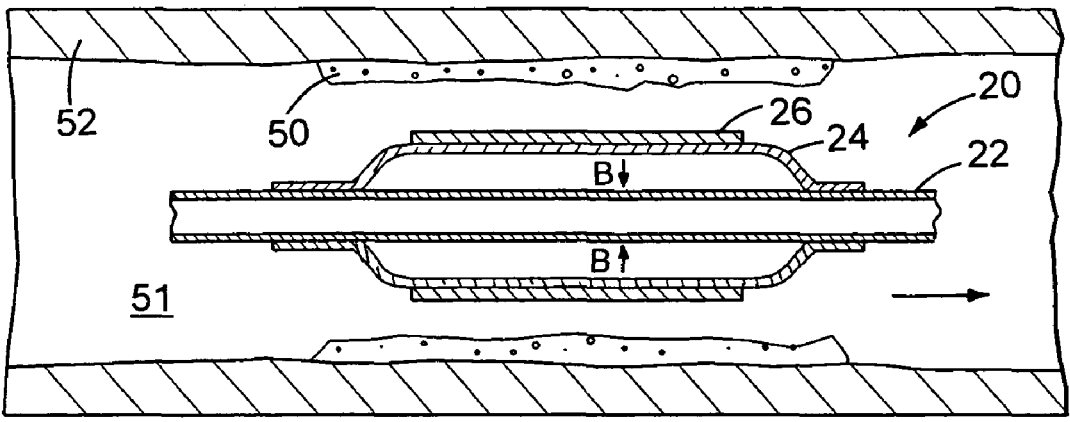
Figure 4:
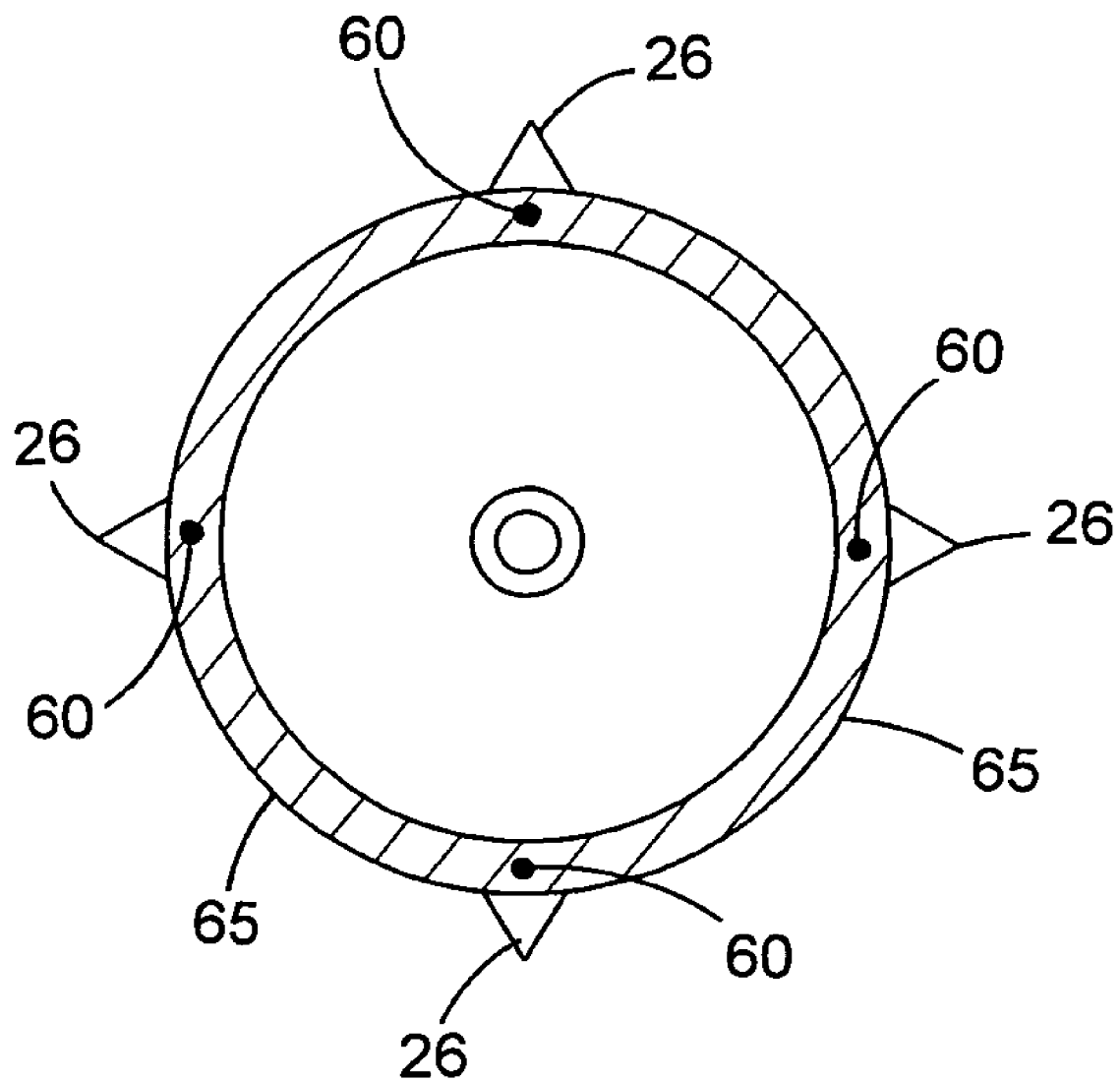
FIG. 4 is an illustration of an embodiment of a medical device system.

Referring to FIGS. 3A, 3B, and 3C, a method of using catheter 20 is shown. Catheter 20 is delivered to a target site 51, e.g., one having a calcified region 50, using conventional methods such as by treading catheter shaft 22 over an emplaced guide wire (not shown). Balloon 24 is unexpanded so that catheter 20 can easily navigate through the patient's body without causing trauma to vessel walls 52. After catheter 20 is properly positioned, expandable balloon 24 is radially expanded (arrows A shown in FIG. 3B), e.g., by introducing a fluid into the interior of the balloon through an inflation lumen (not shown) extending along catheter shaft 22. As expandable balloon 24 is expanded, the one or more cutting elements 26 are advanced radially outward toward calcified region 50 until cutting elements 26 pierce and/or contact calcified region 50. Catheter 20 can be moved (e.g. translated and/or rotated) to provide a desired cutting action to remove, at least in part, calcified region 50 from vessel wall 52. Subsequently, expandable balloon 24 is deflated (arrows B shown in FIG. 3C) so that cutting elements 26 are withdrawn from the vessel wall 52. Catheter 20 is then removed according to conventional methods.

In general, catheter 20 can be used to treat blocked or partially blocked lumens within a patient's body. For example, in certain embodiments, catheter 20 is used to treat blockages in coronary arteries. In some embodiments, catheter 20 is used to treat blockages in the urinary tract. In certain embodiments, catheter 20 is used to treat blockages in the gastrointestinal tract.

The following examples are illustrative and not intended to be limiting.

EXAMPLE 1

A tube for making a four by ten millimeter balloon was extruded to have three layers, a first layer, a second layer, and a third layer. The first and second layers of the tube defined the inner and outer surfaces of the tube and were made from nylon 12 Vestamid L2101F pellets (Degussa Corporation, Parsippany, N.J.). The third layer was sandwiched between the first and second layers and was formed of (90 weight percent) cryogenically ground nylon 12 Vestamid L2101F pellets (Degussa Corporation, Parsippany, N.J.) blended and compounded with (10 weight percent) hexamethyldisilane surface treated 12 nanometer fumed silica particles, AEROSIL® R8200 (Degussa Corporation, Parsippany, N.J.). The first, second, and third layers were co-extruded at a line speed of 77.5 fpm. The co-extrusion conditions were as follows. For the first layer, the melt temperature was 468° F. and the screw (1 inch diameter screw) speed was 7.4 rpm. For the second layer, the melt temperature was 455° F. and the screw (1 inch diameter screw) speed was 10.7 rpm. For the third layer (e.g., the layer between the first and second layers), the melt temperature was 428° F. and the screw (1 inch diameter screw) speed was 7.5 rpm.

The extruded tube was then placed in a four millimeter by 10 millimeter balloon mold that had been preheated to a temperature of 253° F. The tube was then held at both of the ends, and air was injected into the tube at about 190 psi to prevent the tube from collapsing under heat. The tube was heated in the mold for about 3.5 seconds, and then pulled by both ends at a speed of five mm/sec for a distance of 20 millimeters on each end. Each end was then allowed to spring back (e.g., contract) about 1 millimeter. While the tube was pulled, the air pressure inside the tube was increased to about 250 psi and held at that pressure for three seconds. Then the pressure was increased again to 350 psi and held for an additional three seconds. The tube was pulled again at both ends for a distance of five millimeters with a speed of 10 mm/s. The pressure inside the tube during this pulling step was increased to 380 psi. To finish balloon formation, the tube was held at a temperature of 253° F. and a pressure of 380 psi for five seconds within the mold. The mold was then opened to remove the formed balloon. The balloon formed from the extruded tubing had a length of 10 mm, a width of 4 mm and a double wall thickness of 0.0016 inch.

EXAMPLE 2

An extruded tube was formed using the process described above, except the third layer (e.g., the layer between the first and second layers) was replaced with a composite including (15 weight percent) hexamethyldisilane surface treated 12 nanometer fumed silica particles, AEROSIL® R8200 (Degussa Corporation) and (85 weight percent) cryogenically ground nylon 12 Vestamid L2101F pellets (Degussa Corporation, Parsippany, N.J.).

To form a balloon, the extruded tube was placed in a four millimeter by 10 millimeter balloon mold that had been preheated to a temperature of 268° F. The tube was then held at both of the ends, and air was injected into the tube at about 200 psi to prevent the tube from collapsing under heat. The tube was heated in the mold for about 35 seconds, and then pulled by both ends at a speed of 5 mm/sec for a distance of 16 millimeters on each end. Each end was then allowed to spring back (e.g., contract) about 1 millimeter. While the tube was pulled, the air pressure inside the tube was increased to about 250 psi and held at that pressure for 3 seconds. Then the pressure was increased again to 350 psi and held for an additional 3 seconds.

EXAMPLE 3

An extruded tube was formed using the process described in Example 1, except the third layer (e.g., the layer between the first and second layers) was replaced with a composite including (20 weight percent) hexamethyldisilane surface treated 12 nanometer fumed silica particles, AEROSIL® R8200 (Degussa Corporation) and (80 weight percent) cryogenically ground nylon 12 Vestamid L2101F pellets (Degussa Corporation, Parsippany, N.J.).

To form a balloon, the extruded tube was placed in a four millimeter by 10 millimeter balloon mold that had been preheated to a temperature of 262° F. The tube was then held at both of the ends, and air was injected into the tube at about 220 psi to prevent the tube from collapsing under heat. The tube was heated in the mold for about 45 seconds, and then pulled by both ends at a speed of 5 mm/sec for a distance of 18 millimeters on each end. Each end was then allowed to spring back (e.g., contract) about 1 millimeter. While the tube was pulled, the air pressure inside the tube was increased to about 250 psi and held at that pressure for 3 seconds. Then the pressure was increased again to 350 psi and held for an additional 3 seconds.

The tube was pulled again at both ends for a distance of 4 millimeters with a speed of 10 mm/s. The pressure inside the tube during this pulling step was increased to 420 psi. To finish balloon formation, the tube was held at a temperature of 262° F. and a pressure of 420 psi for 5 seconds within the mold. The mold was then opened to remove the formed balloon. The balloon formed from the extruded tube described in this example had a double wall thickness of 0.0017 inch.

EXAMPLE 4

A tube for making a four by ten millimeter balloon was extruded to have three layers, a first layer, a second layer, and a third layer. The first and second layers of the tube defined the inner and outer surfaces of the tube and were made from nylon 12 Vestamid L210F pellets (Degussa Corporation, Parsippany, N.J.). The third layer was sandwiched between the first and second layers and was formed of SEP™ Nanocomposite Nylon, a composite including 5% layered silicate nanocomposite particles. The composite is available from Foster Corporation, Dayville, Conn. The first, second, and third layers were co-extruded at a line speed of 75 fpm. The co-extrusion conditions were as follows. For the first layer, the melt temperature was 453° F. and the screw (1 inch diameter screw) speed was 7.5 rpm. For the second layer, the melt temperature was 461° F. and the screw (1 inch diameter screw) speed was 10.5 rpm. For the third layer (e.g., the layer between the first and second layers), the melt temperature was 441° F. and the screw (1 inch diameter screw) speed was 7.5 rpm.

To form a balloon, the extruded tube was placed in a four millimeter by 10 millimeter balloon mold that had been preheated to a temperature of 250° F. The tube was then held at both of the ends, and air was injected into the tube at about 250 psi to prevent the tube from collapsing under heat. The tube was heated in the mold for about 35 seconds, and then pulled by both ends at a speed of 25 mm/sec for a distance of 22 millimeters on each end. Each end was then allowed to spring back (e.g., contract) about 1 millimeter. While the tube was pulled, the air pressure inside the tube was increased to about 300 psi and held at that pressure for 3 seconds. Then the pressure was increased again to 340 psi and held for an additional 3 seconds.

The tube was pulled again at both ends for a distance of 6 millimeters with a speed of 25 mm/s. The pressure inside the tube during this pulling step was increased to 380 psi. To finish balloon formation, the tube was held at a temperature of 250° F. and a pressure of 380 psi for 5 seconds within the mold. The mold was then opened to remove the formed balloonThe balloon formed from the extruded tube had a double wall thickness of 0.0017 inch.

Other Embodiments

While certain embodiments have been described, other embodiments are also possible.

As an example, while the polymeric material(s) used within the layers forming wall 30 have been described as the same material for all of the layers, in some embodiments, each of the layers can have different polymeric material(s). For example, in a three layer balloon, the first, second, and third layers can each be formed of one or more different polymeric material(s). In some embodiments, the first and second layers are formed of the same polymeric material(s) and the third layer is formed of a different polymeric material.

As an additional example, referring to FIG. 5, while expandable balloons have been described to include a wall having at least one layer formed of a polymeric material(s) and a plurality of additives in the polymeric material(s), in some embodiments, the polymeric materials and plurality of additives can form one or more striped portions 60 of a balloon 65. As a result, striped portions 60 have enhanced mechanical properties and increased resistance to elongation as compared to portions of balloon 65 containing solely polymeric material(s). Cutting elements 26 are attached to balloon 65 over striped portions 60. During expansion of balloon 65, striped portions 60 experience less elongation along the balloon's longitudinal axis. As a result, mechanical stress between cutting elements 26 and balloon 65 is reduced and attachment there between is enhanced.

As an further example, while the polymeric material(s) and additives have been described as being used to form a wall of an expandable balloon, in some embodiments the polymeric material(s) and additives are used to form a wall within any expandable portion of a medical device. For example, in some embodiments, the polymeric material(s) and additives are used to form a wall of an expandable stent. In general, the expandable stent can be of any desired shape and size (e.g., coronary stents, aortic stents, peripheral stents, gastrointestinal stents, urological stents, and neurological stents.) In certain embodiments, a coronary stent can have an expanded diameter of from about two millimeters to about six millimeters. In some embodiments, a peripheral stent can have an expanded diameter of from about five millimeters to about 24 millimeters. In certain embodiments, a gastrointestinal and/or urological stent can have an expanded diameter of from about six millimeters to about 30 millimeters. In some embodiments, a neurological stent can have an expanded diameter of from about two millimeters to about 12 millimeters. The expandable stent can be balloon-expandable, self-expandable, or a combination of both. The expandable stent can be delivered according to conventional methods.

Moreover, the polymeric material(s) and additives can be used to form any portion of the medical device. For example, the polymeric material(s) and additives can be used to form one or more layers of a wall of shaft 22. As a result of including one or more layers having polymeric material(s) and additives within the wall of the shaft, the shaft experiences enhanced mechanical properties, such as, for example, increased stiffness, tensile modulus, and yield stress.

As an additional example, while a medical device has been described has having four cutting elements, a medical device system can have more or less than four (e.g., none, one, two, three, five, six, seven, eight) cutting elements. The cutting elements can be equally and/or unequally spaced around the circumference of an expandable portion (e.g., balloon, stent) of the medical device. For example, for a medical device having six cutting elements spaced about the circumference of the expandable portion, the cutting elements can be spaced at 2 o'clock, 3 o'clock, 4 o'clock, 8 o'clock, 9 o'clock and 10 o'clock. A cutting element located at 3 o'clock is equally spaced with the blades positioned at 2 o'clock and 4 o'clock; but for example, the cutting element at 4 o'clock is unequally spaced with the cutting elements positioned at 3 o'clock and 8 o'clock.

All publications, references, applications, and patents referenced in this application are hereby incorporated by reference in their entirety.

Other embodiments are in the claims.

What is claimed is:

1. A system, comprising:
an expandable medical balloon having a wall formed of a polymeric material and a plurality of particles uniformly dispersed within the polymeric material;
wherein the plurality of particles comprise a material selected from the group consisting of fumed silica, carbon black and combinations thereof;
wherein the plurality of particles are treated to provide surfaces of the plurality of particles with a functional group that covalently bonds the plurality of particles to the polymeric material within the wall of the balloon.

2. The system of claim 1, wherein the plurality of particles are coated with a coupling agent.

3. The system of claim 1, wherein the surface of each of the plurality of particles is plasma-treated.

4. The system of claim 1, wherein the polymeric material is selected from the group consisting of polyesters, polyamides, polyurethanes, polycarbonates, polyolefins, and combinations thereof.

5. The system of claim 1, wherein the polymeric material is selected from the group consisting of ionomers, elastomers, and combinations thereof.

6. The system of claim 1, wherein the wall comprises at most about 50 weight percent of the plurality particles.

7. The system of claim 1, wherein the polymeric material comprises a plurality of polymers.

8. The system of claim 1, wherein the wall comprises multiple layers.

9. The system of claim 1, further comprising a cutting element attached to the wall of the medical balloon.

* * * * *